United States Patent
Sasaki et al.

(10) Patent No.: US 7,446,212 B2
(45) Date of Patent: Nov. 4, 2008

(54) POLYMETHINE ETHERS

(75) Inventors: Nobuaki Sasaki, Yao (JP); Keiki Chichiishi, Yao (JP); Sayuri Wada, Yao (JP); Shigeo Fujita, Yao (JP)

(73) Assignee: Yamamoto Chemicals, Inc., Yao-shi (JP)

( * ) Notice: Subject to any disclaimer, the term of this patent is extended or adjusted under 35 U.S.C. 154(b) by 550 days.

(21) Appl. No.: 10/559,451

(22) PCT Filed: Jun. 16, 2004

(86) PCT No.: PCT/JP2004/008794

§ 371 (c)(1),
(2), (4) Date: Dec. 5, 2005

(87) PCT Pub. No.: WO2005/000814

PCT Pub. Date: Jan. 6, 2005

(65) Prior Publication Data

US 2006/0167272 A1  Jul. 27, 2006

(30) Foreign Application Priority Data

Jun. 25, 2003  (JP) .............................. 2003-181590

(51) Int. Cl.
 *C07D 403/08* (2006.01)
(52) U.S. Cl. .................. 548/455; 548/452; 548/454
(58) Field of Classification Search .................. 548/452, 548/454, 455
See application file for complete search history.

(56) References Cited

U.S. PATENT DOCUMENTS

| 6,261,737 | B1 * | 7/2001 | Fujita et al. | 430/270.1 |
| 6,342,335 | B1 * | 1/2002 | Fujita et al. | 430/270.1 |
| 6,716,993 | B2 * | 4/2004 | Sasaki et al. | 548/454 |
| RE39,105 | E * | 5/2006 | Fujita et al. | 430/270.1 |

FOREIGN PATENT DOCUMENTS

| JP | 2000-226528 A | 8/2000 |
| JP | 2001-64255 A | 3/2001 |
| JP | 2002-52855 A | 2/2002 |

* cited by examiner

*Primary Examiner*—Golam M Shameem
(74) *Attorney, Agent, or Firm*—Birch, Stewart, Kolasch & Birch, LLP

(57) ABSTRACT

The invention provides novel compounds useful as intermediates for the production of polymethine compounds containing a desired counter ion with high purity and in high yields.

Thus provided are polymethine ether compounds of the general formula (I) given below and a method of producing polymethine compounds which comprises bringing those compounds into contact with an acid.

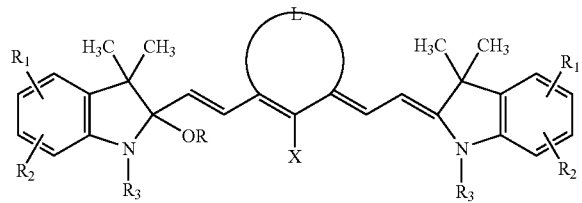

(I)

In the above formula, R represents an alkyl group, an alkoxyalkyl group or an aryl group which may optionally be substituted, $R_1$ and $R_2$ each independently represents a hydrogen atom, halogen atom, nitro group, alkyl group, alkoxyalkyl group, alkoxy group or alkoxyalkoxy group and $R_1$ and $R_2$ may be bound to each other to form a ring; $R_3$ represents an alkyl group, which may optionally be substituted; L is an alkylene group required for the formation of a ring structure; and X represents a hydrogen atom, halogen atom, alkoxy group, aryloxy group, alkylthio group, arylthio group or substituted amino group.

7 Claims, 8 Drawing Sheets

POLYMETHINE ETHERS

TECHNICAL FIELD

The present invention relates to novel polymethine ether compounds and a method of producing polymethine compounds utilizing the same.

BACKGROUND ART

In recent years, polymethine compounds have been in wide use, among others, as light-to-heat converting agents for optical recording media, for near-infrared absorbing filters or plate-making materials for which laser beams are to be utilized. These polymethine compounds generally form a salt structure with a counter ion, and researches have been made concerning polymethine compounds improved in various ways with respect to the counter ion for the purpose of improving the solubility in solvents, the compatibility with resins, the durability and the sensitivity to laser beams.

For producing polymethine compounds containing a desired counter ion species, a method is known which comprises once synthesizing a polymethine compound containing a counter ion species relatively easy to synthesize, for example a perchlorate ion, tetrafluoroborate ion or p-toluenesulfonate ion, dissolving the polymethine compound obtained and a compound containing the desired counter ion species in a solvent, for example dimethylformamide (hereinafter referred to as "DMF") to cause counter ion species interchange in the solvent, as described in Example 1 in Japanese Kokai Publication 2000-302992, for instance.

Further, as is described in Example 1 in Japanese Kokai Publication H11-1626, a synthetic method is known which comprises once synthesizing a polymethine compound containing a counter ion species relatively easy to synthesize, for example a perchlorate ion, tetrafluoroborate ion or p-toluenesulfonate ion, reacting the polymethine compound obtained with an alkali such as caustic soda to give an intermediate compound (hereinafter referred to as "hydroxy compound") resulting from elimination of the counter ion and having a structure represented by the formula (B) given below, and further reacting this hydroxy compound with a compound containing the desired counter ion.

(B)

(In the formula (B), $R_1$, $R_2$, $R_3$, L and X are as defined later herein referring to the formula (I).)

However, as regards the former method, the range of producible counter ion species is limited and, further, the counter ion species exchange is incomplete and it is therefore difficult to obtain, by that method, the high-purity compounds containing a desired counter ion species in high yields. As for the latter method, on the other hand, the hydroxy compounds are very unstable and, therefore, this method of producing polymethine compounds using those hydroxy compounds is not suitable as an industrial production method since the purity and yield of the products are low and a complicated purification process is required for obtaining high-purity products.

As a compound structurally close to the polymethine ether compounds of the invention, there is the compound (A) having the structure shown below as described in Dyes and Pigments, 46 (2000), 164. However, there is no description about the use thereof, among others. If the compound (A) is used to produce the corresponding polymethine compound, the polymethine compound obtained will show an absorption wavelength range fairly longer ($\geqq 1000$ nm) than the general-purpose semiconductor laser wavelength range and, further, the raw materials for the production thereof are special and the production cost is increased accordingly, hence the industrial use value will be restricted.

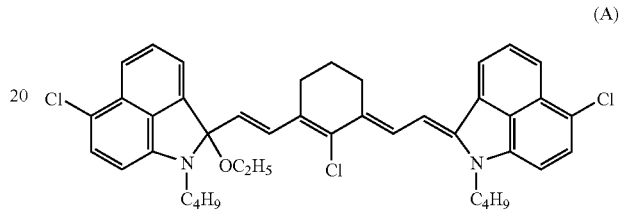

(A)

DISCLOSURE OF INVENTION

It is an object of the present invention to provide novel polymethine ether compounds useful as intermediates for the production of polymethine compounds containing a desired counter ion.

As a result of various investigations made in an attempt to accomplish the above object, the present inventors found that certain novel polymethine ether compounds are stable and can be handled with ease and when they are reacted with an acid, high-quality polymethine compounds with an acidic residue as the counter ion can be readily produced in high yields. This finding has now led to completion of the present invention.

In a first aspect, the present invention provides polymethine ether compounds represented by the following general formula (I):

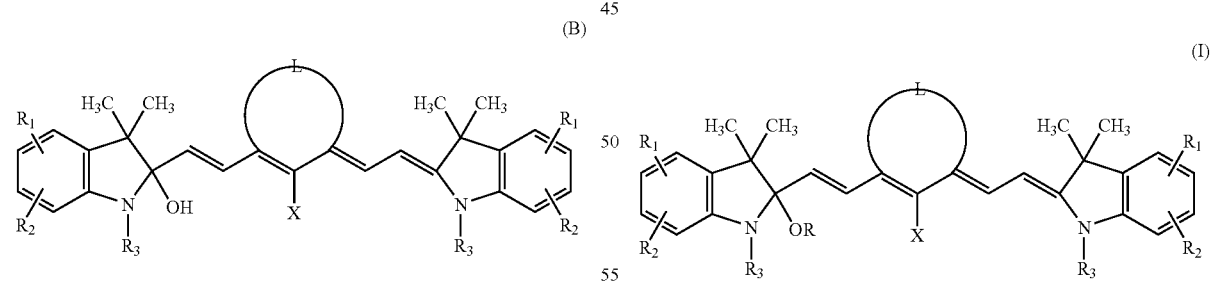

(I)

wherein R represents an alkyl group, an alkoxyalkyl group or an aryl group which may optionally be substituted, $R_1$ and $R_2$ each independently represents a hydrogen atom, halogen atom, nitro group, alkyl group, alkoxyalkyl group, alkoxy group or alkoxyalkoxy group and $R_1$ and $R_2$ may be bound to each other to form a ring; $R_3$ represents an alkyl group, which may optionally be substituted; L is an alkylene group required for the formation of a ring structure; and X represents a hydrogen atom, halogen atom, alkoxy group, aryloxy group, alkylthio group, arylthio group or substituted amino group.

DETAILED DESCRIPTION OF THE INVENTION

Figure 1:
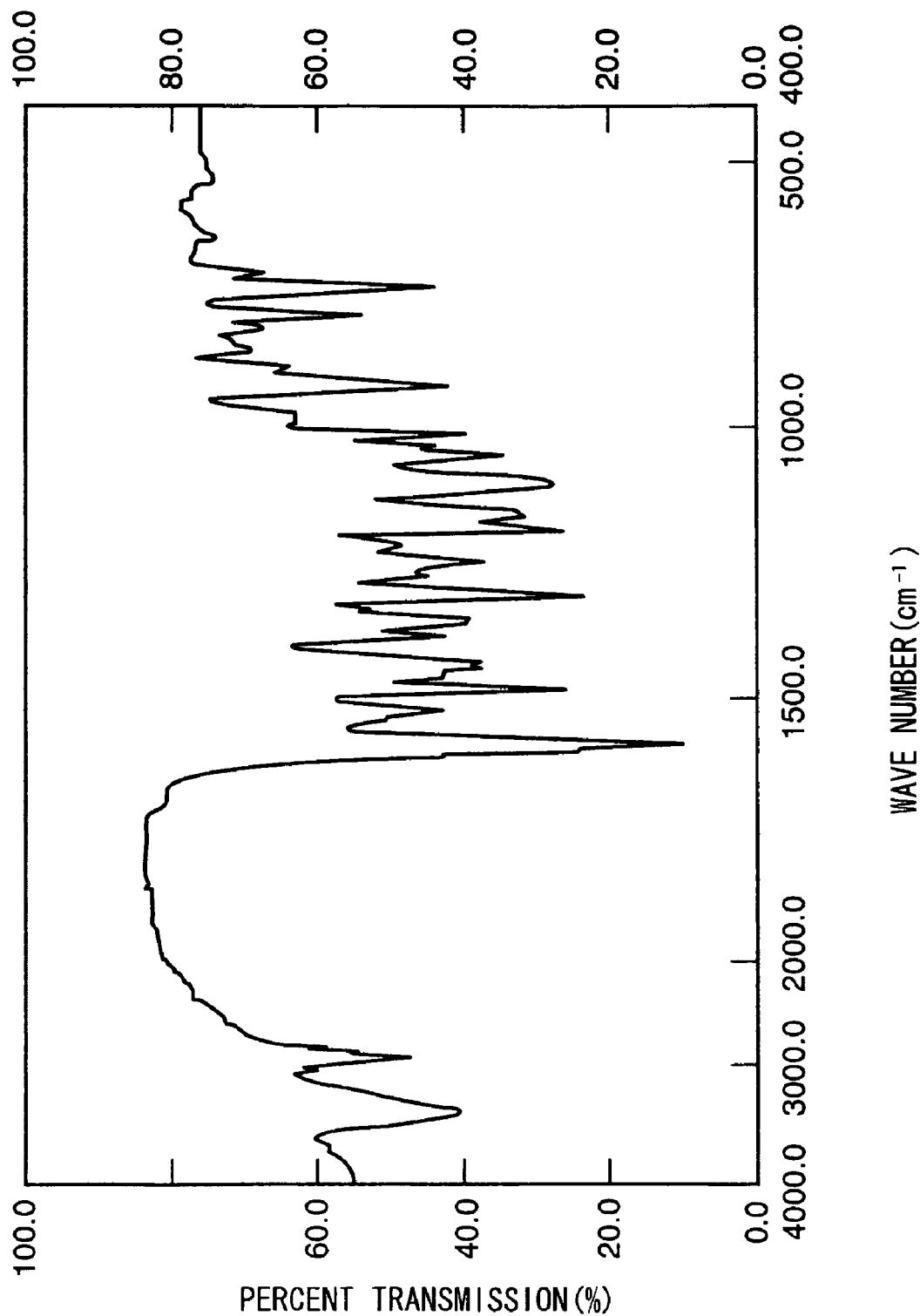
FIG. 1 is an IR absorption spectrum of the polymethine ether compound of Example 1.

In the following, the present invention is described in detail.

[Polymethine Ether Compounds]

First, the polymethine ether compounds represented by the general formula (I) given below in accordance with the first aspect of the invention are described.

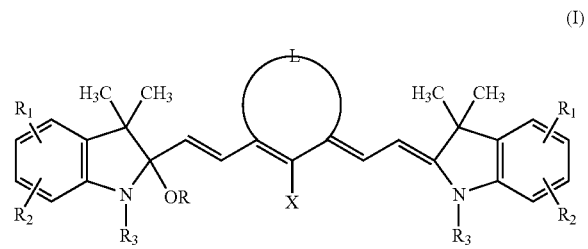

(I)

In the above formula, R represents an alkyl group, an alkoxyalkyl group or an aryl group which may optionally be substituted, $R_1$ and $R_2$ each independently represents a hydrogen atom, halogen atom, nitro group, alkyl group, alkoxyalkyl group, alkoxy group or alkoxyalkoxy group and $R_1$ and $R_2$ may be bound to each other to form a ring; $R_3$ represents an alkyl group, which may optionally be substituted; L is an alkylene group required for the formation of a ring structure; and X represents a hydrogen atom, halogen atom, alkoxy group, aryloxy group, alkylthio group, arylthio group or substituted amino group.

(Substituent R)

When R is an alkyl group, it is preferably a straight or branched alkyl group containing 1-8 carbon atoms, particularly preferably a straight or branched alkyl group containing 1-4 carbon atoms. As examples, there may be mentioned methyl, ethyl, n-propyl, isopropyl, n-butyl, isobutyl, sec-butyl, tert-butyl, n-pentyl, isopentyl, neopentyl, n-hexyl, isohexyl, sec-hexyl, 2-ethylbutyl, n-heptyl, isoheptyl, sec-heptyl, n-octyl and 2-ethylhexyl.

When R is an alkoxyalkyl group, it is preferably one containing 2-8 carbon atoms in total, particularly preferably one containing 2-4 carbon atoms in total. As examples, there may be mentioned methoxymethyl, 2-methoxyethyl, 3-methoxypropyl, 2-ethoxymethyl, 2-ethoxyethyl, 2-propoxyethyl and 2-butoxyethyl.

When R is an optionally substituted aryl group, it may be an optionally substituted phenyl group or an optionally substituted naphthyl group but preferably is an optionally substituted phenyl group. Each substituent may be an alkyl, amino, nitro, alkoxy or hydroxy group or a halogen atom, and preferably is an alkyl group containing 1-4 carbon atoms or an alkoxy group containing 1-4 carbon atoms.

As examples of R when it is an alkyl-substituted phenyl, there may be mentioned 2-methylphenyl, 3-methylphenyl, 4-methylphenyl, 2,3-dimethylphenyl, 2,4-dimethylphenyl, 3,4-dimethylphenyl, 2,5-dimethylphenyl, 2,6-dimethylphenyl, 2-ethylphenyl, 3-ethylphenyl, 4-ethylphenyl, 2,3-diethylphenyl, 2,4-diethylphenyl, 3,4-diethylphenyl, 2,5-diethylphenyl and 2,6-diethylphenyl.

As examples of R when it is an alkoxy-substituted phenyl, there may be mentioned 2-methoxyphenyl, 3-methoxyphenyl, 4-methoxyphenyl, 2,3-dimethoxyphenyl, 2,4-dimethoxyphenyl, 3,4-dimethoxyphenyl, 2,5-dimethoxyphenyl and 2,6-dimethoxyphenyl.

(Substituents $R_1$ and $R_2$)

As the halogen atom represented by $R_1$ and/or $R_2$, there may be mentioned F, Cl, Br, 0 and so forth. However, Cl and Br are preferred, and Cl is particularly preferred.

As for the alkyl group represented by $R_1$ and $R_2$, straight or branched alkyl groups containing 1-8 carbon atoms are preferred, and straight or branched alkyl groups containing 1-4 carbon atoms are particularly preferred. As examples, there may be mentioned methyl, ethyl, n-propyl, isopropyl, n-butyl, isobutyl, sec-butyl, n-pentyl, isopentyl, neopentyl, n-hexyl, isohexyl, sec-hexyl, 2-ethylbutyl, n-heptyl, isoheptyl, sec-heptyl, n-octyl and 2-ethylhexyl.

As for the alkoxyalkyl group represented by $R_1$ and $R_2$, alkoxyalkyl groups containing 2-8 carbon atoms in total are preferred, and alkoxyalkyl groups containing 2-4 carbon atoms in total are particularly preferred. As examples, there may be mentioned 2-methoxyethyl, 3-methoxypropyl, 4-methoxybutyl, 2-ethoxyethyl, 2-n-butoxyethyl, 2-n-propoxyethyl, 2-isopropoxyethyl, 2-n-butoxyethyl, 3-ethoxypropyl, 3-n-propoxypropyl, 4-ethoxybutyl, 4-n-propoxybutyl, 2-methoxy-2-ethoxyethyl and 2-ethoxy-2-ethoxyethyl.

As for the alkoxy group represented by $R_1$ and $R_2$, straight or branched alkoxy groups containing 1-8 carbon atoms are preferred, and straight or branched alkoxy groups containing 1-4 carbon atoms are particularly preferred. As examples, there may be mentioned methoxy, ethoxy, n-propoxy, isopropoxy, n-butoxy, isobutoxy, sec-butoxy, n-pentyloxy, isopentyloxy, neopentyloxy, n-hexyloxy, isohexyloxy, sec-hexyloxy, 2-ethylbutoxy, n-heptyloxy, isoheptyloxy, sec-heptyloxy, n-octyloxy and 2-ethylhexyloxy.

As for the alkoxyalkoxy group represented by $R_1$ and $R_2$, alkoxyalkoxy groups containing 2-8 carbon atoms in total are preferred, and alkoxyalkoxy groups containing 2-4 carbon atoms in total are particularly preferred. Examples are 2-methoxyethoxy, 3-methoxypropoxy, 4-methoxybutoxy, 2-ethoxyethoxy, 2-n-butoxyethoxy, 2-n-propoxyethoxy, 2-isopropoxyethoxy, 2-n-butoxyethoxy, 3-ethoxypropoxy, 3-n-propoxypropoxy, 4-ethoxybutoxy, 4-n-propoxybutoxy, 2-methoxy-2-ethoxyethoxy and 2-ethoxy-2-ethoxyethoxy.

Preferred as $R_1$ and $R_2$ are a hydrogen atom, alkyl groups containing 1-8 carbon atoms, alkoxyalkyl groups containing 2-8 carbon atoms in total, alkoxy groups containing 1-8 carbon atoms, alkoxyalkoxy groups containing 2-8 carbon atoms in total, or cyclic structures formed by $R_1$ and $R_2$ bound to each other; particularly preferred are a hydrogen atom, alkyl groups containing 1-4 carbon atoms, alkoxyalkyl group containing 2-4 carbon atoms in total, alkoxy groups containing 1-4 carbon atoms and alkoxyalkoxy groups containing 2-4 carbon atoms in total.

As the ring structure formed by $R_1$ and $R_2$ bound to each other, there may be mentioned a benzene ring, hydrocarbon ring or oxygen-containing cyclic ring formed by $R_1$ and $R_2$ bound to each other, together with the benzene ring carbon atoms bound to $R_1$ and $R_2$, respectively, preferably a benzene ring, a hydrocarbon ring containing 5-7 carbon atoms, or an oxygen-containing heterocycle containing 3-6 carbon atoms, more preferably a benzene, cyclopentane or dioxolane ring. As examples, there may be mentioned a benzene ring, cyclopentane ring, cyclohexane ring, cycloheptane ring, dioxolane ring and dioxane ring.

(Substituent $R_3$)

When $R_3$ is an unsubstituted alkyl group, it is preferably a straight or branched alkyl group containing 1-18 carbon atoms, particularly preferably a straight or branched alkyl group containing 1-8 carbon atoms. Examples are methyl, ethyl, n-propyl, isopropyl, n-butyl, isobutyl, sec-butyl, n-pentyl, isopentyl, neopentyl, n-hexyl, isohexyl, sec-hexyl, 2-ethylbutyl, n-heptyl, isoheptyl, sec-heptyl, n-octyl, 2-ethylhexyl, n-decyl, n-dodecyl, n-pentadecyl and n-octadecyl.

As the substituted alkyl group represented by $R_3$, there may be mentioned alkoxyalkyl groups, sulfoalkyl groups and carboxyalkyl groups, among others. Alkoxyalkyl groups containing 2-8 carbon atoms in total are preferred, and those containing 2-4 carbon atoms in total are particularly preferred. As examples of the alkoxyalkyl groups, there may be mentioned 2-methoxyethyl, 3-methoxypropyl, 4-methoxybutyl, 2-ethoxyethyl, 2-n-butoxyethyl, 2-n-propoxyethyl, 2-isopropoxyethyl, 2-n-butoxyethyl, 3-ethoxypropyl, 3-n-propoxypropyl, 4-ethoxybutyl, 4-n-propoxybutyl, 2-methoxy-2-ethoxyethyl and 2-ethoxy-2-ethoxyethyl.

Preferred as $R_3$ are alkyl groups containing 1-8 carbon atoms or alkoxyalkyl groups containing 2-8 carbon atoms in total and, among them, alkyl groups containing 1-8 carbon atoms or alkoxyalkyl groups containing 2-4 carbon atoms in total are particularly preferred.

(Substituent L)

L is a substituted or unsubstituted alkylene group and forms a ring together with three carbon atoms, namely the carbon atom bound to X and the carbon atoms on both sides thereof. Preferred as L are ethylene, propylene, butylenes, 2-oxapropylene, 2-thiapropylene, 2-methylpropylene and 2-tert-butylpropylene and, among them, ethylene, propylene and butylenes are particularly preferred.

(Substituent X)

The halogen atom represented by X includes F, Cl, Br and I, among others. Cl and Br are preferred, and Cl is particularly preferred.

The alkoxy group represented by X is preferably an alkoxy group containing 1-8 carbon atoms, particularly preferably an alkoxy group containing 1-4 carbon atoms. Examples are methoxy, ethoxy, propoxy, butoxy, pentoxy, hexyloxy, heptyloxy and octyloxy, among others.

The alkylthio group represented by X is preferably an alkylthio group containing 1-8 carbon atoms, particularly preferably an alkylthio group containing 1-4 carbon atoms. Examples are methylthio, ethylthio, propylthio, butylthio, pentylthio, hexylthio, heptylthio and octylthio, among others.

The aryloxy group represented by X is preferably a phenyloxy group, which may optionally have an alkyl group containing 1-8 carbon atoms as a substituent, particularly preferably a phneyloxy or methylphenyloxy. As examples, there may be mentioned phenyloxy, methylphenyloxy and tert-butylphenyloxy.

The arylthio group represented by X is preferably a phenylthio group, which may optionally have an alkyl group containing 1-8 carbon atoms as a substituent, particularly preferably phenylthio and methylphenylthio. As examples, there may be mentioned phenylthio, methylphenylthio and tert-butylphenylthio.

Preferred as the substituent(s) on the substituted amino group represented by X are alkyl groups containing 1-8 carbon atoms and a phenyl group and, among them, alkyl groups containing 1-4 carbon atoms and a phenyl group are particularly preferred. As examples of X, there may be mentioned methylamino, ethylamino, propylamino, butylamino, dimethylamino, diethylamino, dipropylamino, dibutylamino, phenylamino and diphenylamino, among others.

Preferred as X are a hydrogen atom, Cl, Br, an alkoxy group containing 1-8 carbon atoms, an alkylthio group containing 1-8 carbon atoms, a phenyloxy group optionally having an alkyl group(s) containing 1-8 carbon atoms as a substituent(s), a phenylthio group optionally having an alkyl group(s) containing 1-8 carbon atoms as a substituent(s), and a substituted amino group optionally having an alkyl group(s) containing 1-8 carbon atoms and/or a phenyl group(s) as a substituent(s). Particularly preferred are Cl, an alkoxy group containing 1-4 carbon atoms, an alkylthio group containing 1-4 carbon atoms, a phenyloxy group optionally having an alkyl group(s) containing 1-4 carbon atoms as a substituent(s), a phenylthio group optionally having an alkyl group(s) containing 1-4 carbon atoms as a substituent(s) and a substituted amino group optionally having an alkyl group(s) containing 1-8 carbon atoms and/or a phenyl group(s) as a substituent(s).

(Specific Examples of the Compound of the Invention)

Preferred specific examples of the polymethine ether compounds of the invention as represented by the general formula (I) are shown below. However, the compounds of the invention are not limited to these.

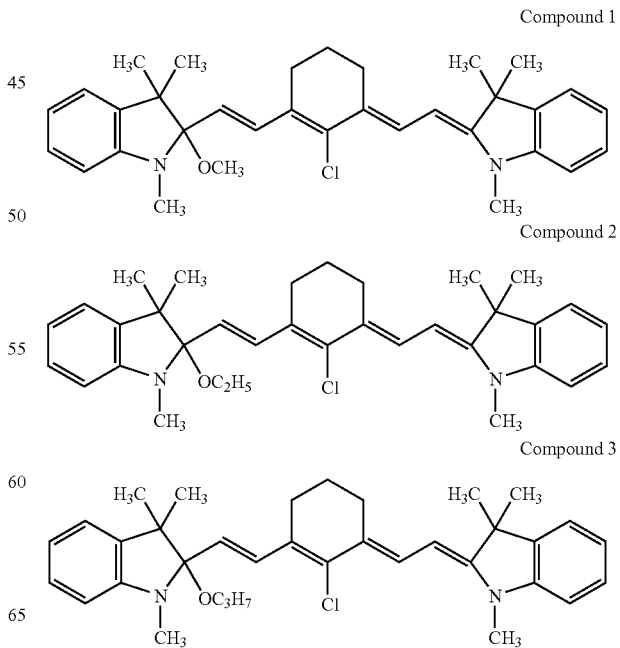

Compound 1

Compound 2

Compound 3

-continued

Compound 4 through Compound 18: chemical structures.

-continued
Compound 19
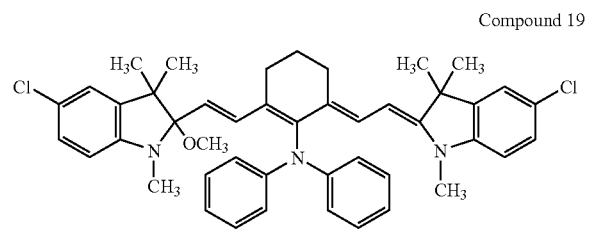
Compound 20
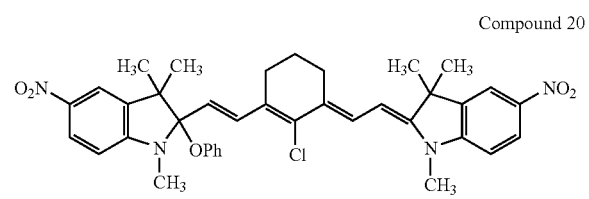
Compound 21
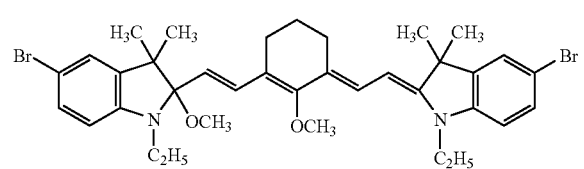
Compound 22
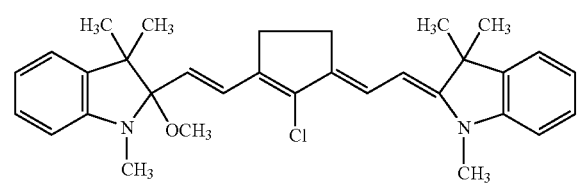
Compound 23
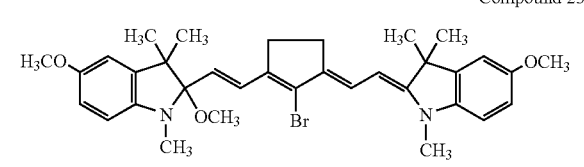
Compound 24
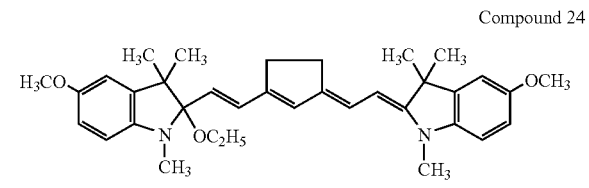
Compound 25
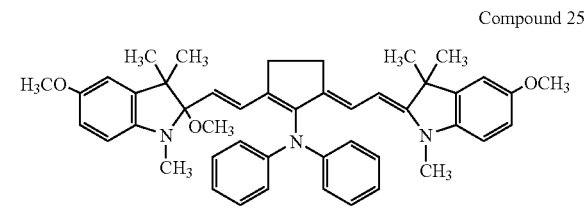
-continued
Compound 26
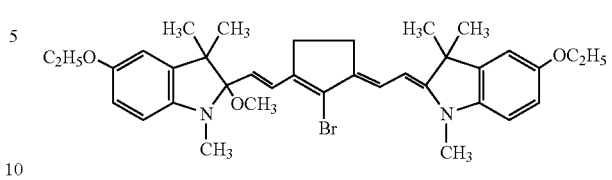
Compound 27
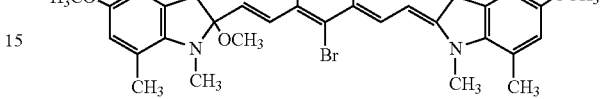
Compound 28
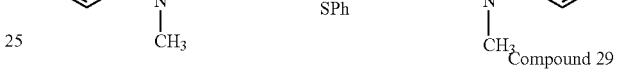
Compound 29
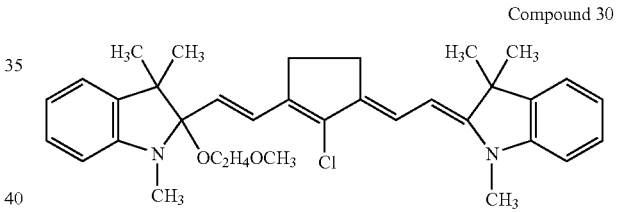
Compound 30
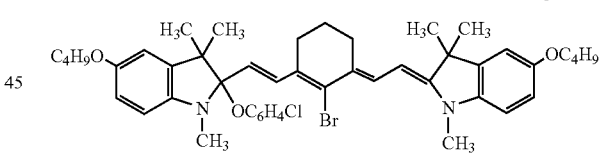
Compound 31
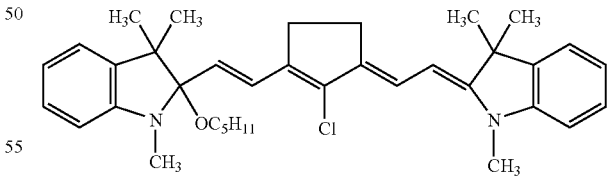
Compound 32
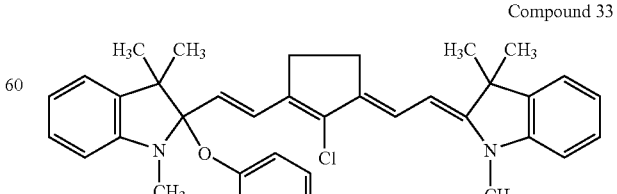
Compound 33
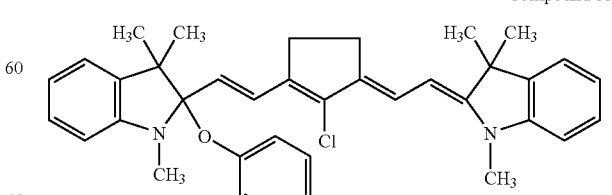

-continued

Compound 34
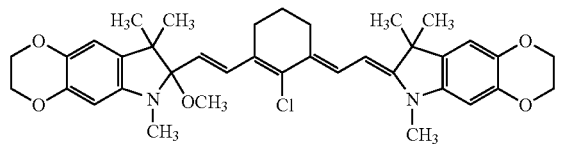

Compound 35
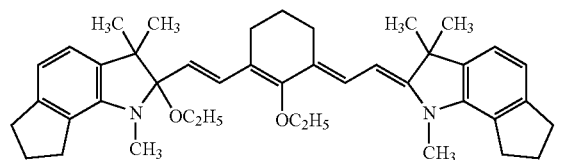

Compound 36
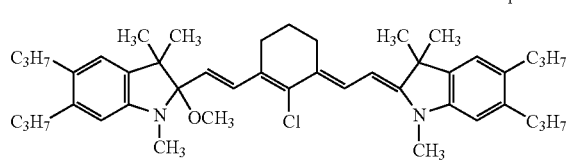

Compound 37
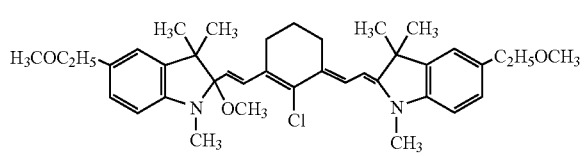

Compound 38
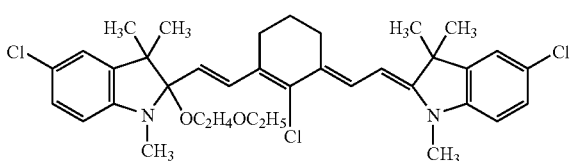

Compound 39
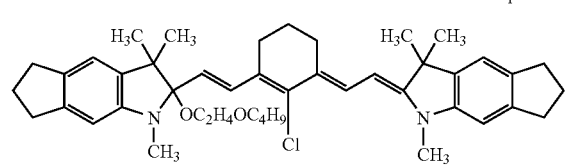

[Method of Producing the Polymethine Ether Compounds]

The polymethine ether compounds (I) of the invention can be produced, for example, by reacting a polymethine compound represented by the general formula (II) given below with an alkali metal alkoxide or alkali metal aryloxide represented by the general formula (III) given below in an organic solvent.

(II)
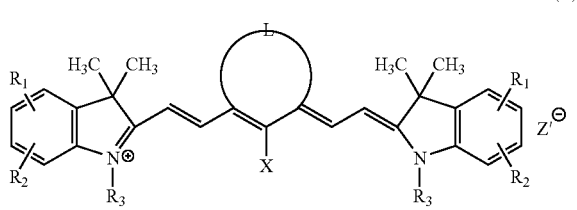

(In the formula, $R_1$ to $R_3$, L and X are as defined above and $Z'^-$ represents an acidic residue.)

MOR (III)

(In the formula, M represents an alkali metal and R is as defined above.)

In the above formula (II), $Z'^-$ represents an acidic residue, for example $F^-$, $Cl^-$, $Br^-$, $I^-$, $BrO_4^-$, $ClO_4^-$, $BF_4^-$, $PF_6^-$, $SbF_6^-$, $CF_3CO_2^-$, $CH_3CO_2^-$, $CF_3SO_3^-$, $CH_3SO_3^-$, benzenecarbonate, benzenesulfonate, p-toluenesulfonate (hereinafter abbreviated as $TsO^-$, naphthalenecarbonate, naphthalenedicarbonate, naphthalenesulfonate or naphthalenedisulfonate. In particular, $Cl^-$, $Br^-$, $I^-$, $ClO_4^-$, $BF_4^-$, $PF_6^-$, $SbF_6^-$, $CF_3CO_2^-$, $CF_3SO_3^-$, $CH_3SO_3^-$, benzenecarbonate, benzenesulfonate and $TsO^-$ are preferred, and $ClO_4^-$, $BF_4^-$ and $TsO^-$ are particularly preferred.

In the above reaction, M is an alkali metal such as sodium or potassium.

As the organic solvent, there may be mentioned, among others, alcohols such as methanol, ethanol, n-propanol, isopropanol and n-butanol, ethers such as tetrahydrofuran and dioxane, esters such as methyl acetate, ethyl acetate and butyl acetate, aromatic hydrocarbons such as benzene, toluene and xylene, halogenated hydrocarbons such as dichlormethane, trichloromethane, dichloroethane and trichloroethane, and aprotic polar solvents such as dimethylformamide, dimethylacetamide and dimethyl sulfoxide.

As for the quantity ratio between the compound represented by the general formula (II) and the compound represented by the general formula (III), the latter is generally used in an amount of about 1-30 moles, preferably about 2-10 moles, per mole of the former.

The organic solvent is generally used in an amount of about 2-30 liters, preferably about 5-20 liters, per mole of the compound represented by the general formula (II).

The above reaction can smoothly proceed generally at about 0-100° C., preferably at about 10-70° C., and will be generally complete in several minutes to about 10 hours.

After the reaction, the desired product can be readily isolated by collection by filtration, followed by washing. It can be purified with ease by the conventional purifying means, such as recrystallization and/or column separation.

The above-mentioned compound represented by the general formula (II) can be synthesized by the method described in Japanese Kokai Publication 2000-226528, for instance.

[Method of Producing the Final Product Polymethine Compounds]

The polymethine compounds represented by the formula (IV):

(IV)
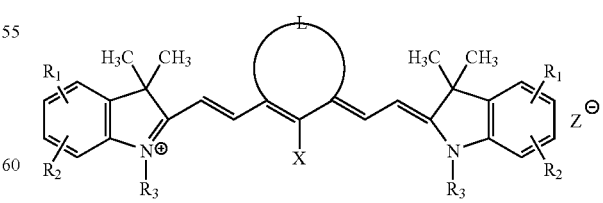

(wherein $R_1$ to $R_3$, L and X are as defined above general formula (I) and $Z^-$ represents an acidic residue) which have a desired $Z^-$, can then be produced from the ether compounds of general formula (I), for example, by reacting an ether compound represented by the formula (I) with an acid containing the desired Z in an organic solvent.

As $Z^-$, there may be mentioned, among others, halogen ions such as $F^-$, $Cl^-$, $Br^-$ and $I^-$, alkylsulfonate ions such as $CH_3SO_3^-$, $CF_3SO_3^-$ and $C_2H_5SO_3^-$, arylsulfonate ions such as benzenesulfonate and p-toluenesulfonate (hereinafter abbreviated as $TsO^-$), naphthalenesulfonate ions such as 2-naphthalenesulfonate ion, 1-hydroxy-4-naphthalenesulfonate ion and 2,3-naphthalenedisulfonate ion, alkylcarboxylate ions such as $CH_3CO_2^-$, $C_2H_5CO_2^-$, $C_3H_7CO_2^-$, $CF_3CO_2^-$ and $C_2F_5CO_2^-$, arylcarboxylate ions such as benzoate ion and 3-hydroxybenzoate ion, naphthalenecarboxylate ions such as 2-naphthalenecarboxylate ion, 1-hydroxy-4-naphthalenecarboxylate ion and 2,3-naphthalenedicarboxylate ion, organoboron ions such as triphenyl butyl borate ion and tetraphenyl borate ion, organometal complex ions such as benzenedithiol nickel complex ion, $BrO_4^-$, $ClO_4^-$, $BF_4^-$, $PF_6^-$, $SbF_6^-$, etc.

The organic solvent includes alcohols such as methanol, ethanol, n-propanol, isopropanol and n-butanol, ethers such as tetrahydrofuran and dioxane, esters such as methyl acetate, ethyl acetate and butyl acetate, aromatic hydrocarbons such as benzene, toluene and xylene, halogenated hydrocarbons such as dichlormethane, trichloromethane, dichloroethane and trichloroethane, and aprotic polar solvents such as dimethylformamide, dimethylacetamide and dimethyl sulfoxide.

The desired Z-containing acid may be a proton donor acid or an electron acceptor acid.

The desired Z-containing proton donor acid includes, among others, hydrohalic acids such as HF, HCl, HBr and HI, alkylsulfonic acids such as $CH_3SO_3H$, $CF_3SO_3H$ and $C_2H_5SO_3H$, arylsulfonic acids such as benzenesulfonic acid and p-toluenesulfonic acid, naphthalenesulfonic acids such as 2-naphthalenesulfonic acid, 1-hydroxy-4-naphthalenesulfonic acid and 2,3-naphthalenedisulfonic acid, alkylcarboxylic acids such as $CH_3CO_2H$, $C_2H_5CO_2H$, $C_3H_7CO_2H$, $CF_3CO_2H$ and $C_2F_5CO_2H$, arylcarboxylic acids such as benzoic acid and 3-hydroxybenzoic acid, naphthalenecarboxylic acids such as 2-naphthalenecarboxylic acid, 1-hydroxy-4-naphthalenecarboxylic acid and 2,3-naphthalenedicarboxylic acid, $HBrO_4$, $HClO_4$, $HBF_4$, $HPF_6$ and $HSbF_6$.

The desired Z-containing electron acceptor acid includes, among others, organoborate salts such as triphenyl butyl borate salts and tetraphenyl borate salts, organic dithiol metal complex salts such as benzenedithiol nickel complex salts, zinc chloride and aluminum chloride.

As for the quantity ratio between the compound represented by the general formula (I) and the acid containing the desired Z, the latter is generally used in an amount of about 0.5-5 moles, preferably about 1-2 moles, per mole of the former.

The organic solvent is generally used in an amount of about 2-30 liters, preferably about 5-20 liters, per mole of the compound represented by the general formula (I).

The above reaction proceeds smoothly generally at a temperature not higher than 100° C., preferably 10-50° C., and will be complete generally in several minutes to about 10 hours.

After the reaction, the desired product can be readily isolated by collection by filtration, followed by washing. Further, it can be purified with ease by the conventional means, for example by recrystallization and/or column separation.

EXAMPLES

The following examples illustrate the present invention more specifically. These examples are, however, by no means limitative of the scope of the invention.

Example 1

Production of a Polymethine Ether Compound (Specific Example Compound (1))

A compound represented by the general formula (II) (each of $R_1$ and $R_2$=hydrogen atom, $R_3$=methyl, L=propylene, X=Cl, $Z'^-=ClO_4^-$; 3.79 g) and 1.76 g of a compound represented by the general formula (III) (M=Na, R=methyl) were added to 150 ml of methanol, the mixture was stirred at 20-25° C. for 3 hours, the resulting crystalline precipitate was filtered off, washed with methanol and recrystallized from acetone to give 2.68 g of Specific Example Compound (1).

The elemental analysis data and melting point of this compound were as follows.

| Elemental analysis ($C_{33}H_{39}ClN_2O$): MW = 515.13 | | | |
|---|---|---|---|
| | C | H | N |
| Calculated (%) | 76.94 | 7.63 | 5.44 |
| Found (%) | 76.88 | 7.69 | 5.48 |
| Melting point (° C.): | 159-162° C. (decomposition) | | |

An IR spectrum of the compound obtained is shown in FIG. 1.

Example 2

Production of a Polymethine Ether Compound (Specific Example Compound (2))

The procedure of Example 1 was followed in the same manner except that the compound of general formula (III) as used was the one with M=Na and R=ethyl (2.21 g), to give 2.82 g of Specific Example Compound (2).

The elemental analysis data and melting point of this compound were as follows.

| Elemental analysis ($C_{34}H_{41}ClN_2O$): MW = 529.15 | | | |
|---|---|---|---|
| | C | H | N |
| Calculated (%) | 77.17 | 7.81 | 5.29 |
| Found (%) | 77.08 | 7.79 | 5.26 |
| Melting point (° C.): | 150-153° C. (decomposition) | | |

Figure 2:
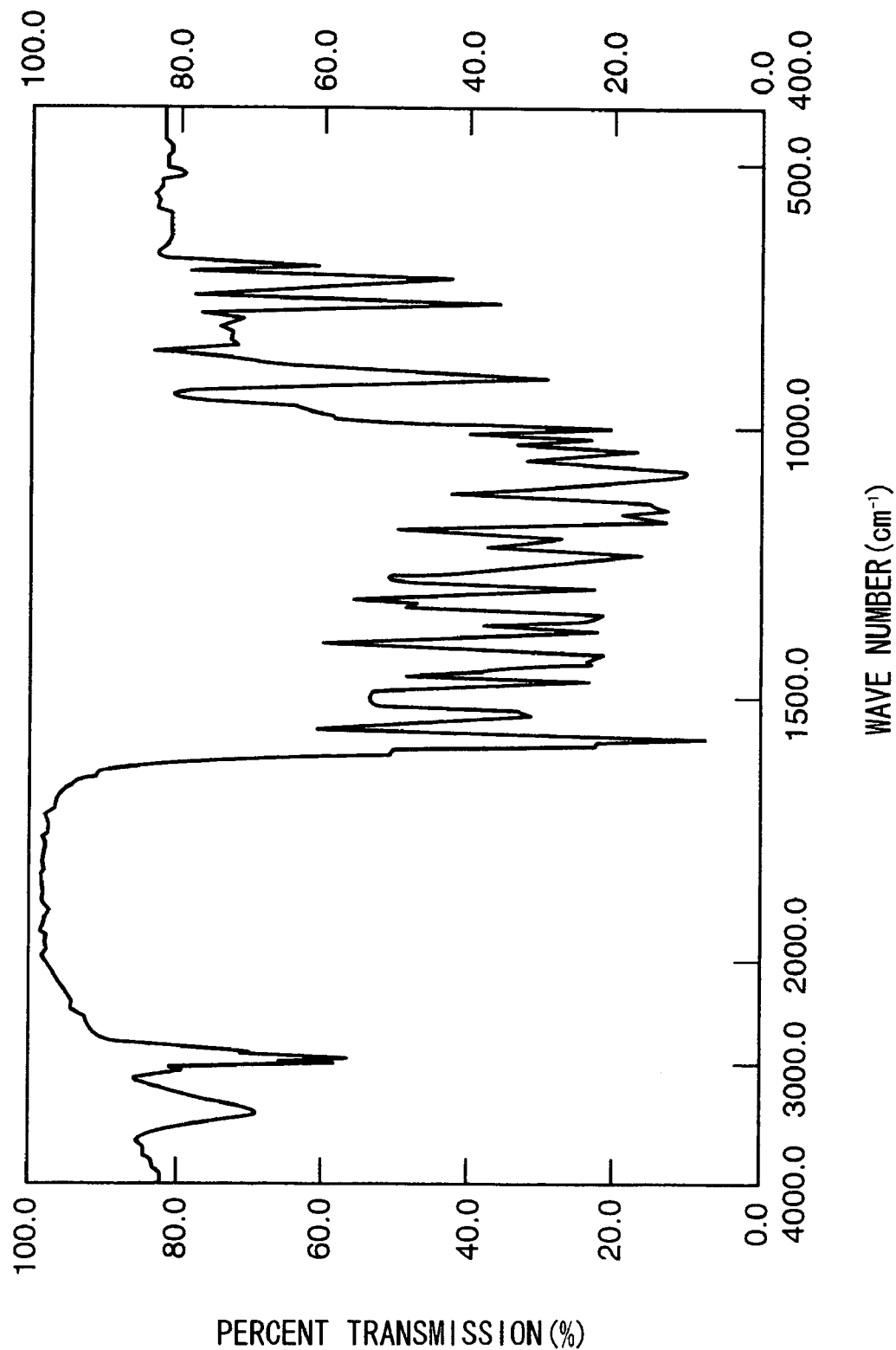
FIG. 2 is an IR absorption spectrum of the polymethine ether compound of Example 2.

An IR spectrum of the compound obtained is shown in FIG. 2.

Example 3

Production of a Polymethine Ether Compound (Specific Example Compound (6))

The procedure of Example 1 was followed in the same manner except that the compound of general formula (II) as used was the one with each of $R_1$ and $R_2$=hydrogen atom, $R_3$=n-propyl, L=propylene, X=Cl, $Z'^-=ClO_4^-$ (4.16 g), to give 2.80 g of Specific Example Compound (6).

The elemental analysis data and melting point of this compound were as follows.

Elemental analysis ($C_{37}H_{47}ClN_2O$): MW = 571.23

|  | C | H | N |
|---|---|---|---|
| Calculated (%) | 77.80 | 8.29 | 4.90 |
| Found (%) | 77.88 | 8.35 | 4.92 |
| Melting point (° C.): | | 97-100° C. | |

Figure 3:
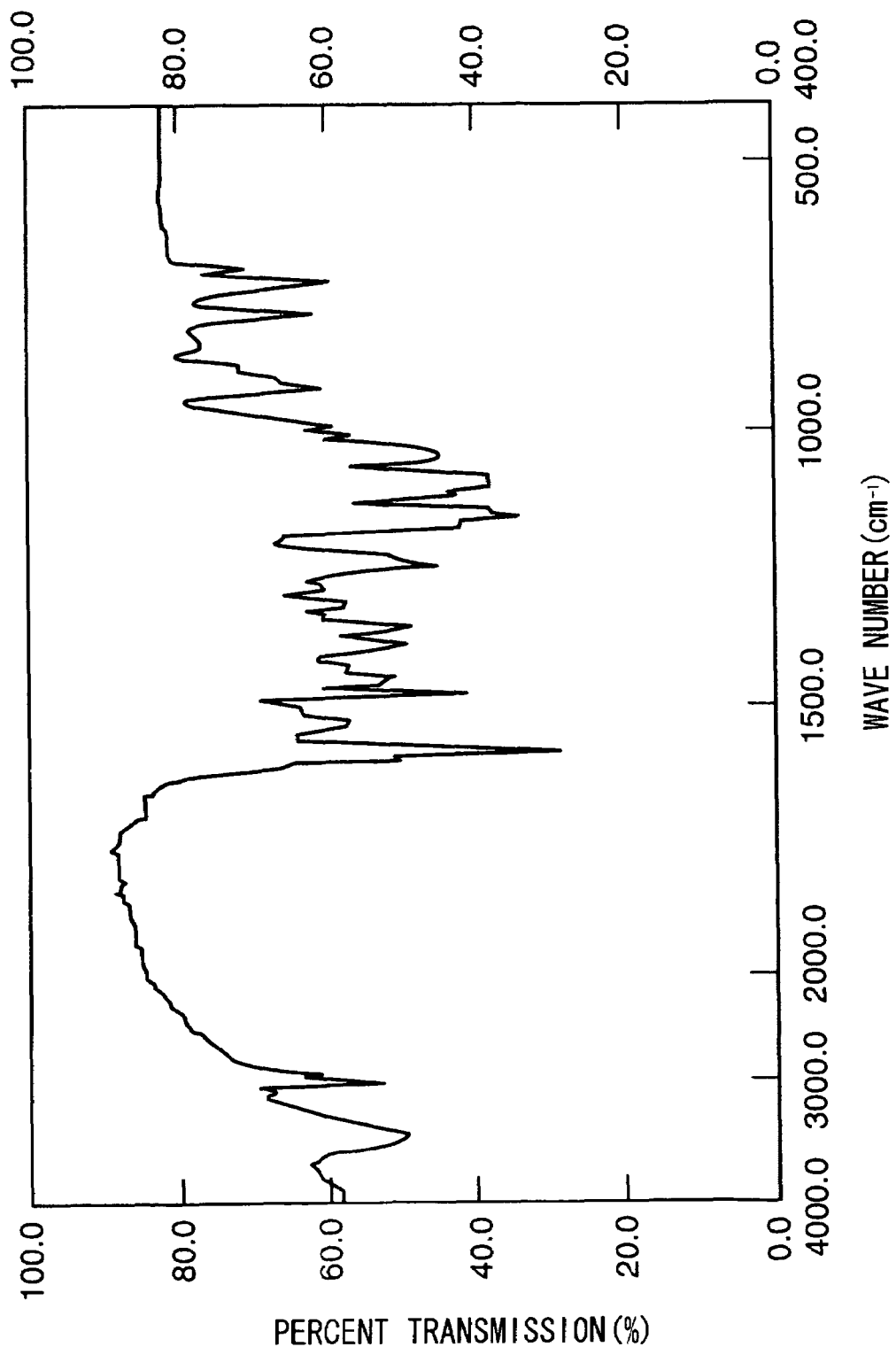
FIG. 3 is an IR absorption spectrum of the polymethine ether compound of Example 3.

An IR spectrum of the compound obtained is shown in FIG. 3.

Example 4

A polymethine Ether Compound (Synthesis of Specific Example Compound (12))

The procedure of Example 1 was followed in the same manner except that the compound of general formula (II) as used was the one with $R_1$=5-methoxy, $R_2$=7-methyl, $R_3$=methoxyethyl, L=propylene, X=Cl, $Z'^-$=$BF_4^-$ (4.86 g) and that the compound of general formula (III) as used was the one with M=Na and R=ethyl (2.21 g), to give 2.90 g of Specific Example Compound (12).

The elemental analysis data and melting point of this compound were as follows.

Elemental analysis ($C_{42}H_{57}ClN_2O_5$): MW = 705.37

|  | C | H | N |
|---|---|---|---|
| Calculated (%) | 71.52 | 8.15 | 3.97 |
| Found (%) | 71.36 | 8.19 | 3.94 |
| Melting point (° C.): | | 143-145° C. | |

Figure 4:
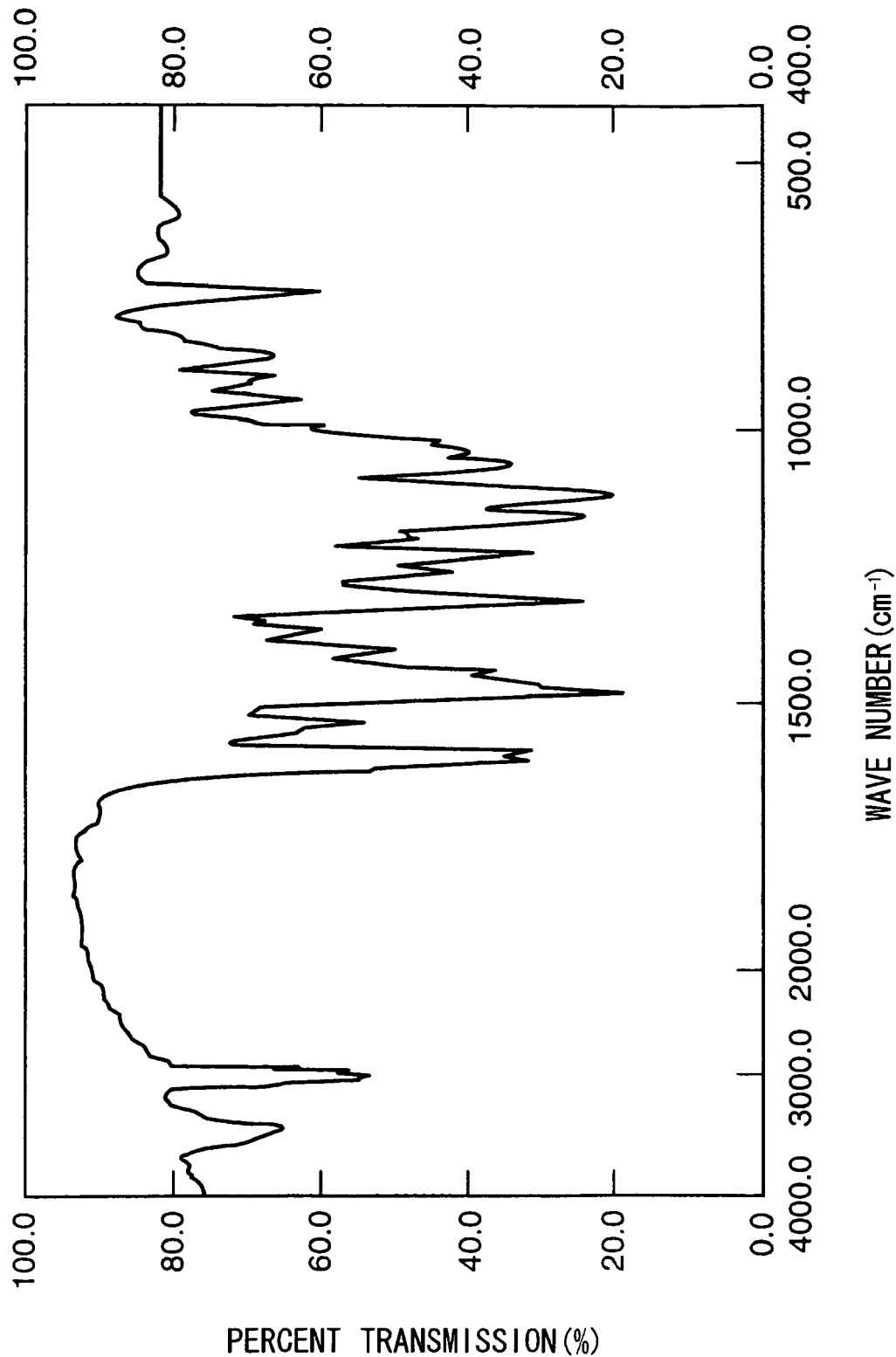
FIG. 4 is an IR absorption spectrum of the polymethine ether compound of Example 4.

An IR spectrum of the compound obtained is shown in FIG. 4.

Example 5

A polymethine Ether Compound (Synthesis of Specific Example Compound (16))

The procedure of Example 1 was followed in the same manner except that the compound of general formula (II) as used was the one with $R_1$ and $R_2$=5,6-methylenedioxy, $R_3$=methyl, L=propylene, X=Cl, $Z'^-$=$ClO_4^-$ (4.37 g), to give 2.83 g of Specific Example Compound (16).

The elemental analysis data and melting point of this compound were as follows.

Elemental analysis ($C_{35}H_{39}ClN_2O_5$): MW = 603.15

|  | C | H | N |
|---|---|---|---|
| Calculated (%) | 69.70 | 6.52 | 4.64 |
| Found (%) | 59.56 | 6.49 | 4.58 |
| Melting point (° C.): | | 175-177° C. | |

Figure 5:
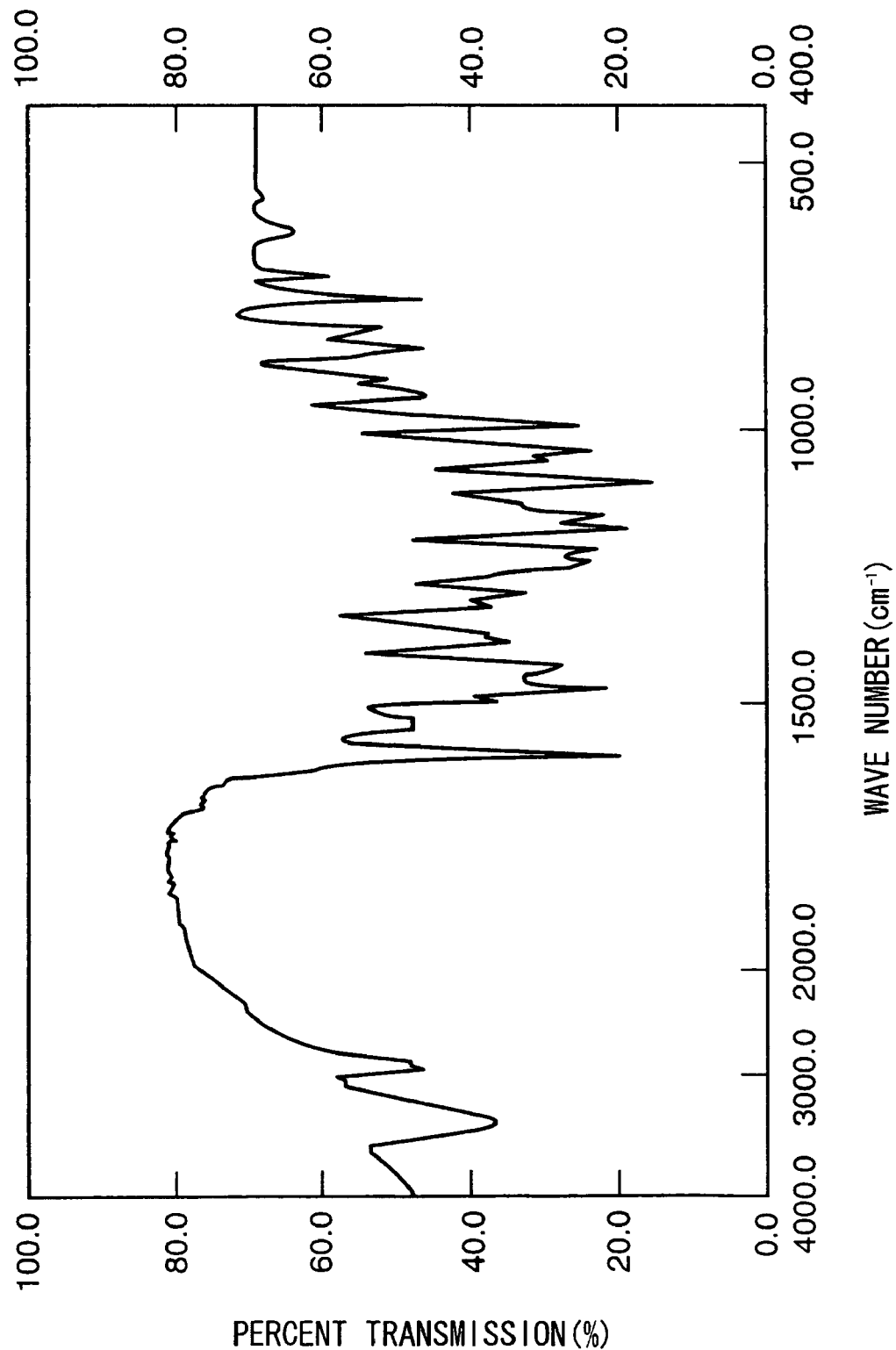
FIG. 5 is an IR absorption spectrum of the polymethine ether compound of Example 5.

An IR spectrum of the compound obtained is shown in FIG. 5.

Example 6

A polymethine Ether Compound (Synthesis of Specific Example Compound (17))

The procedure of Example 1 was followed in the same manner except that the compound of general formula (II) as used was the one with $R_1$ and $R_2$=5,6-benzo, $R_3$=methyl, L=propylene, X=Cl, $Z'^-$=$TsO^-$ (4.91 g), to give 2.54 g of Specific Example Compound (17).

The elemental analysis data and melting point of this compound were as follows.

Elemental analysis ($C_{41}H_{43}ClN_2O$): MW = 615.25

|  | C | H | N |
|---|---|---|---|
| Calculated (%) | 80.04 | 7.04 | 4.55 |
| Found (%) | 80.04 | 7.05 | 4.61 |
| Melting point (° C.): | | 184-187° C. | |

Figure 6:
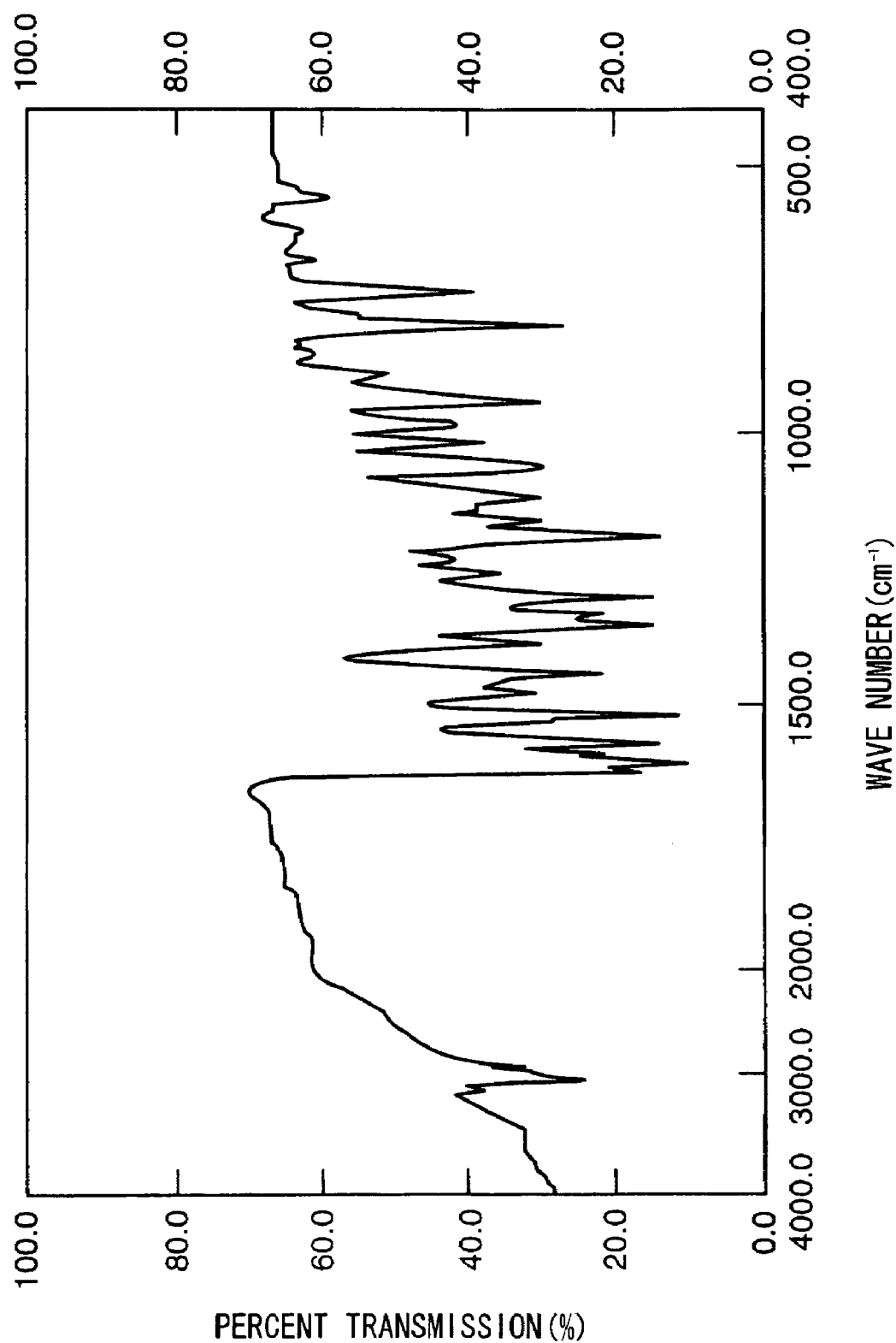
FIG. 6 is an IR absorption spectrum of the polymethine ether compound of Example 6.

An IR spectrum of the compound obtained is shown in FIG. 6.

Example 7

A polymethine Ether Compound (Synthesis of Specific Example Compound (22))

The procedure of Example 1 was followed in the same manner except that the compound of general formula (II) as used was the one with each of $R_1$ and $R_2$=hydrogen atom, $R_3$=methyl, L=ethylene, X=Cl, $Z'^-$=$ClO_4^-$ (3.70 g), to give 2.62 g of Specific Example Compound (22).

Elemental analysis ($C_{32}H_{37}ClN_2O$): MW = 501.10

|  | C | H | N |
|---|---|---|---|
| Calculated (%) | 76.70 | 7.44 | 5.59 |
| Found (%) | 76.62 | 7.50 | 5.59 |
| Melting point (° C.): | | 205-207° C. | |

Figure 7:
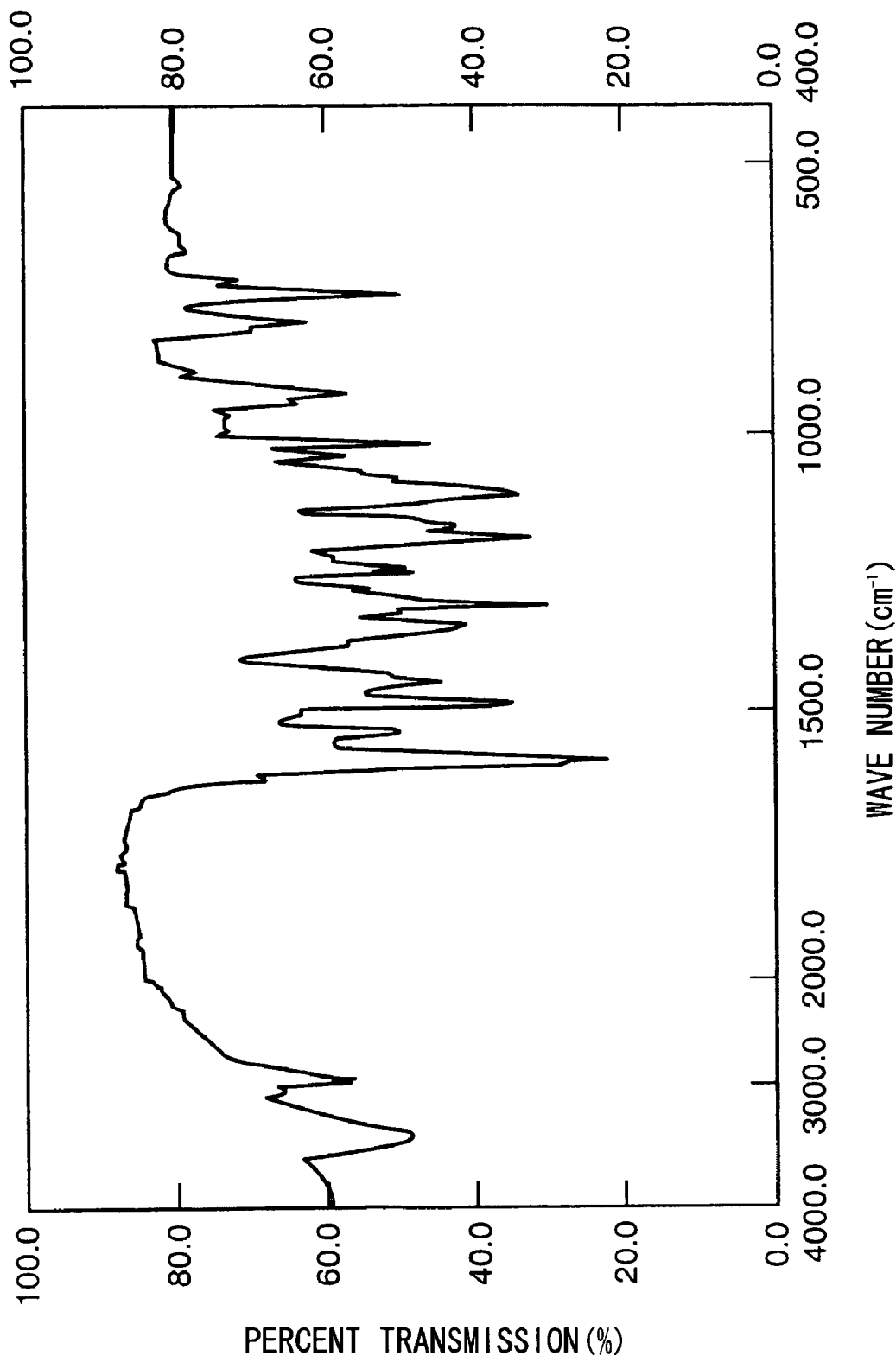
FIG. 7 is an IR absorption spectrum of the polymethine ether compound of Example 7.

An IR spectrum of the compound obtained is shown in FIG. 7.

Example 8

Synthesis of a Polymethine Compound

Specific Example Compound (12) (5.00 g) was added to 50 ml of methanol, and 15 ml of a methanol solution containing 3.00 g of pentafluoropropionic acid was added dropwise thereto with stirring at 25-30° C. After 2 hours of stirring at the same temperature, the methanol was distilled off from the reaction mixture using an evaporator, and 50 ml of ethyl acetate was then added to the residue. The resulting crystalline precipitate was filtered off, washed with ethyl acetate and dried to give 4.98 g of a compound having the structure given below (yield: 85.2%).

The elemental analysis data, melting point, absorption maximum wavelength (λmax) and gram extinction coefficient (eg) of this compound were as follows.

| Elemental analysis ($C_{43}H_{52}ClF_5N_2O_6$): MW = 823.3 | | | |
|---|---|---|---|
| | C | H | N |
| Calculated (%) | 62.73 | 6.37 | 3.40 |
| Found (%) | 62.81 | 6.40 | 3.38 |
| Melting point (° C.): | 198-199° C. | | |
| λmax: | 822 nm (diacetone alcohol solution) | | |
| εg: | $2.75 \times 10^5$ ml/g·cm | | |

Figure 8:
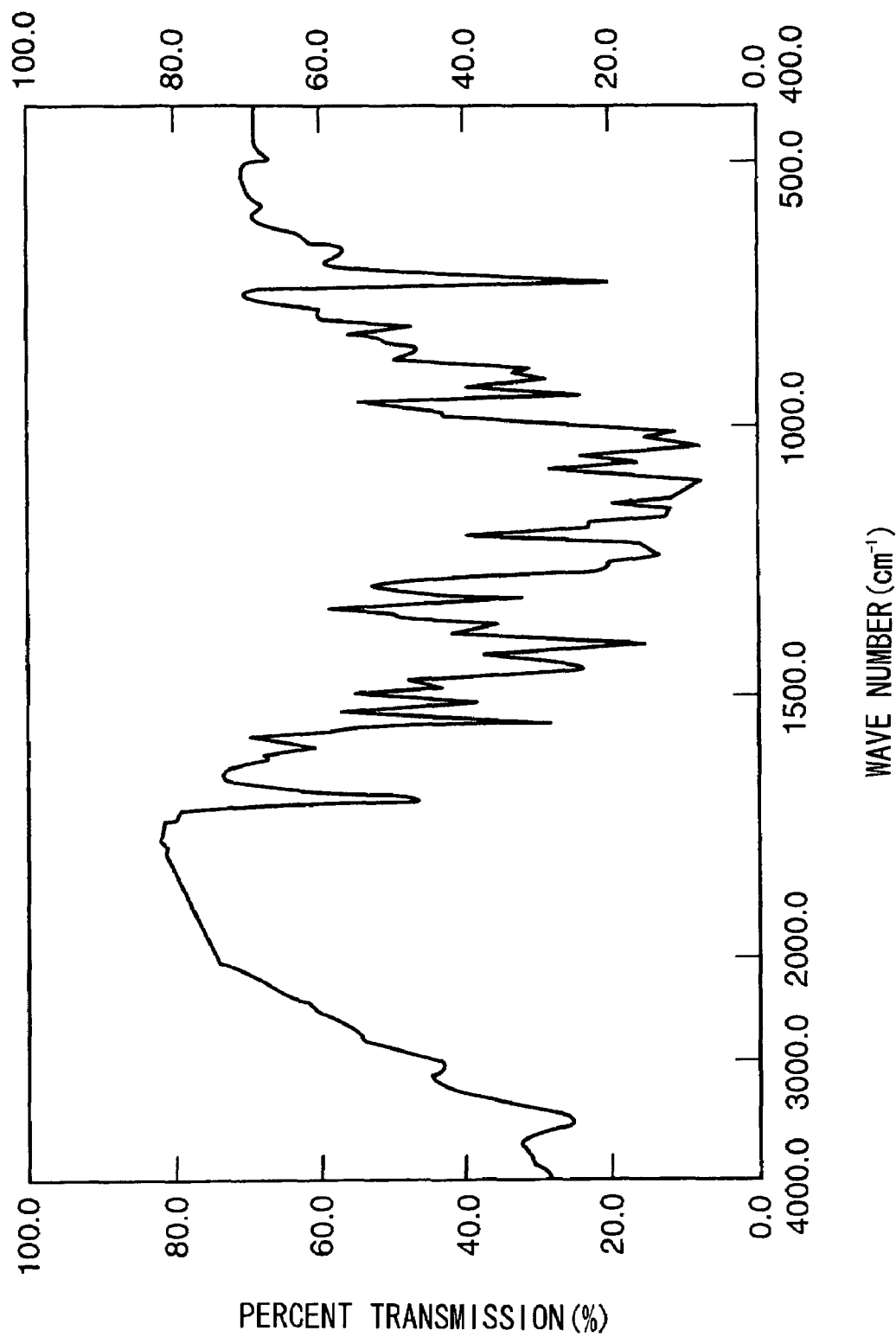
FIG. 8 is an IR absorption spectrum of the polymethine compound of Example 8.

An IR spectrum of the compound obtained is shown in FIG. 8.

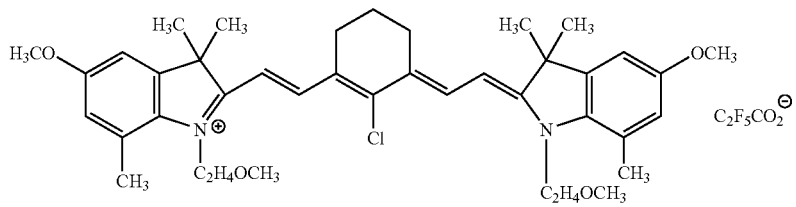

Comparative Example 1

A Hydroxy Compound and Production of a Polymethine Compound Using the Same

As described in Example 1 in Japanese Kokai Publication H11-1626, 15.0 g of a compound of general formula (II) with $R_1$=5-methoxy, $R_2$=7-methyl, $R_3$=methoxyethyl, L=propylene, X=Cl, $Z'^-$=$BF_4^-$ was added to 150 ml of DMF, and the mixture was stirred at 20-25° C. for 0.5 hour to effect dissolution. The solution was green, and the λmax of the DMF solution was 824 nm. To this DMF solution was added 4.8 g of a 50% aqueous solution of caustic soda, followed by 1.0 hour of stirring at 25-30° C. The color of the DMF solution changed from green to yellowish brown (the λmax of the DMF solution changed to 434 nm and the absorption at 824 nm disappeared).

The reaction mixture was poured into 1500 g of ice water, and the resulting crystalline precipitate was filtered off, washed with water and dried to give 12.51 g of an ocher compound.

This compound gave the following elemental analysis data and was identified as a hydroxy compound of the formula (B) given hereinabove.

| Elemental analysis ($C_{40}H_{53}ClN_2O_5$): MW = 677.31 | | | |
|---|---|---|---|
| | C | H | N |
| Calculated (%) | 70.93 | 7.89 | 4.14 |
| Found (%) | 70.48 | 7.99 | 4.19 |

A 3.39-g portion of the hydroxy compound obtained was dissolved in 35 ml of methanol, and 15 ml of a methanol solution containing 2.12 g of pentafluoropropionic acid was added dropwise thereto with stirring at 25-30° C. After 2 hours of stirring at the same temperature, the methanol was distilled off from the reaction mixture using an evaporator, and 35 ml of ethyl acetate was added to the residue. The resulting crystalline precipitate was filtered off, washed with ethyl acetate and dried to give 2.28 g (yield: 55.3%) of a compound having the same structure as the product obtained in Example 8.

The absorption maximum wavelength (λmax) and gram extinction coefficient (eg) of this compound were as follows.

λmax: 822 nm (diacetone alcohol solution)

εg: $0.98 \times 10^5$ ml/g·cm

As compared with Example 8 in which a polymethine ether compound of the invention was used, the yield of the polymethine compound was low and the purity of the compound obtained was low (εg ratio relative to the compound of Example 8: 0.36).

INDUSTRIAL APPLICABILITY

The compounds of the invention are useful intermediates for the production of polymethine compounds containing a desired counter ion with high purity and in high yields.

The novel polymethine ether compounds are stable and can be handled with ease and, when reacted with an acid, can give high-quality polymethine compounds with the acidic residue as the counter ion in high yields.

The invention claimed is:

1. A polymethine ether compound represented by the general formula (I):

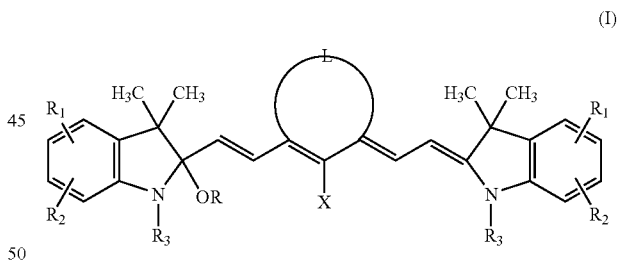

(I)

wherein R represents an alkyl group, an alkoxyalkyl group or an aryl group which may optionally be substituted, $R_1$ and $R_2$ each independently represents a hydrogen atom, halogen atom, nitro group, alkyl group, alkoxyalkyl group, alkoxy group or alkoxyalkoxy group and $R_1$ and $R_2$ may be bound to each other to form a ring; $R_3$ represents an alkyl group, which may optionally be substituted; L is an alkylene group required for the formation of a ring structure; and X represents a hydrogen atom, halogen atom, alkoxy group, aryloxy group, alkylthio group, arylthio group or substituted amino group.

2. A polymethine ether compound according to claim 1, wherein R is an alkyl group containing 1-8 carbon atoms, an alkoxyalkyl group containing 2-8 carbon atoms in total or a phenyl which may optionally have an alkyl group containing 1-4 carbon atoms or an alkoxy group containing 1-4 carbon atoms as a substituent, $R_1$ and $R_2$ each is a hydrogen atom, an alkyl group containing 1-8 carbon atoms, an alkoxyalkyl group containing 2-8 carbon atoms in total or an alkoxy group containing 1-8 carbon atoms or $R_1$ and $R_2$ are bound to each other and form, together with the benzene ring carbon atoms bound to $R_1$ and $R_2$, respectively, a benzene ring, a hydrocarbon ring containing 5-7 carbon atoms or an oxygen-containing heterocycle containing 3-6 carbon atoms, and $R_3$ is an alkyl group containing 1-18 carbon atoms or an alkoxyalkyl group containing 2-8 carbon atoms in total.

3. A polymethine ether compound according to claim 1, wherein L is an alkylene group containing 2-4 carbon atoms.

4. A polymethine ether compound according to claim 1, wherein X is a hydrogen atom, Cl, Br, an alkoxy group containing 1-8 carbon atoms or a diphenylamino.

5. A polymethine ether compound according to claim 2, wherein L is an alkylene group containing 2-4 carbon atoms.

6. A polymethine ether compound according to claim 2, wherein X is a hydrogen atom, Cl, Br, an alkoxy group containing 1-8 carbon atoms or a diphenylamino.

7. A polymethine ether compound according to claims 3, wherein X is a hydrogen atom, Cl, Br, an alkoxy group containing 1-8 carbon atoms or a diphenylamino.

* * * * *